United States Patent [19]

Pfenninger

[11] Patent Number: 5,306,247
[45] Date of Patent: Apr. 26, 1994

[54] BALLOON CATHETER

[75] Inventor: Susanne Pfenninger, New York, N.Y.

[73] Assignee: Schneider (Europe) A.G., Bulach, Switzerland

[21] Appl. No.: 987,937

[22] Filed: Dec. 9, 1992

[30] Foreign Application Priority Data

Dec. 11, 1991 [EP] European Pat. Off. ........ 91203259.6

[51] Int. Cl.⁵ .............................................. A61M 29/00
[52] U.S. Cl. ........................................ 604/96; 606/194
[58] Field of Search ........................... 128/656–658; 604/91, 101, 102; 606/192, 194

[56] References Cited

U.S. PATENT DOCUMENTS

| 4,748,982 | 6/1988 | Horzewski et al. ........... 606/192 X |
| 4,782,834 | 11/1988 | Maguire et al. . | |
| 4,943,278 | 7/1990 | Euteneuer et al. ................. 604/96 |
| 4,944,745 | 7/1990 | Sogard et al. ................. 606/194 |
| 5,061,273 | 10/1991 | Yock ........................... 604/96 X |
| 5,154,725 | 10/1992 | Leopold ....................... 606/194 |
| 5,156,594 | 10/1992 | Keith ............................ 604/96 |
| 5,180,367 | 1/1993 | Kontos et al. ................ 606/194 |
| 5,192,295 | 3/1993 | Danforth et al. .............. 606/194 |
| 5,209,729 | 5/1993 | Hofmann et al. . | |
| 5,232,445 | 8/1993 | Bonzel ............................ 604/96 |

FOREIGN PATENT DOCUMENTS 9220397 11/1992 World Int. Prop. O. .

OTHER PUBLICATIONS

Niederhauser et al., U.S. patent application Ser. No. 07/904,231 filed Jun. 25, 1992.

Primary Examiner—C. Fred Rosenbaum
Assistant Examiner—Frank Wilkens
Attorney, Agent, or Firm—Peter C. Richardson; Lawrence C. Akers; Eric M. Lee

[57] ABSTRACT

A balloon catheter with a shaft having a balloon located proximate a distal end thereof, with the shaft having a lumen through which a balloon is supplied and a lumen through which a guide wire is passed. The shaft consists of a proximal area and a distal area, with the shaft being made of a stiffer material in the proximal shaft area than in the distal shaft area. In one embodiment of the proximal shaft area, the supply lumen and the guide lumen are coaxially disposed. In one embodiment of the distal shaft area, the supply lumen and the guide lumen are biaxially disposed. An /utlet opening for the guide wire is disposed in the shaft in the proximal area of the catheter wherein a guide wire passing through the opening can be advanced into the guide lumen and towards the balloon for passage through the distal end.

4 Claims, 6 Drawing Sheets ic BALLOON CATHETER

BACKGROUND OF THE INVENTION

This invention relates to a balloon catheter with a shaft having at its distal end a balloon. The shaft has one lumen through which the balloon is supplied and another lumen through which a guide wire is passed. The guide wire functions to guide and control the catheter in use. The shaft consists of a proximal area and a distal area, with the shaft being made of a stiffer material in the proximal area. The lumen for the guide wire is coaxially located in the proximal area of the shaft so that the lumen for supplying the balloon surrounds the lumen for the guide wire like a ring. In the distal area the shaft is made of a more flexible material and the lumen for supplying the balloon and the lumen for the guide wire are arranged biaxially side by side.

A balloon catheter of this type is disclosed, for example, in German Utility Patent 9,106,499. The balloon catheter disclosed there is used together with a guide catheter and a guide wire for percutaneous transluminal coronary recanalization. The catheter is inserted into a blood vessel through a puncture in the skin and is advanced through the blood vessel to an arteriosclerotic occlusion in coronary vessels, for example. Then the occlusion is widened with the inflatable balloon at the end of the catheter.

The shaft of this known catheter is composed of two lengths. The proximal length on the operating end is made of an especially rigid material and is also arranged coaxially, i.e., according to the "tube-in-a-tube" system, which leads to an especially rigid shaft in this area.

The distal length of the shaft on the end remote from the manipulator is made of an especially flexible material and is designed so the two lumens in the shaft, namely the channel for supplying the balloon and the channel for receiving the guide 7ire, are arranged side by side in a joint shaft sheathing. This yields a more flexible design, so the two measures together, namely the flexible material and the more flexible design, yield a shaft that can adapt to all blood vessel shapes.

This arrangement should achieve the effect that, on the one hand, the distal end of the catheter with the balloon folded up can be inserted easily into the convoluted passages of the coronary vessels but, on the other hand, the shearing forces for advancing the catheter can be transmitted well in the proximal rigid section of the shaft at the same time.

If the proximal section is not rigid enough, the shaft will give to the side under the shearing forces as the catheter is advanced, and especially high frictional forces will develop between the catheter and the side wall in the areas where the catheter yields to the side. Some of the shearing force applied to the shaft is thus lost and is no longer available for pushing through a vascular occlusion, for example. This also means that some of the sensory perception is lost for the treating physician since some of the resistance perceived by the physician in advancing the catheter is due to uncontrolled frictional forces rather than resistance that should be taken into account by the physician in performing the treatment. This lateral yielding of the catheter shaft in advancing the catheter also means that the tip of the catheter, the balloon, does not cover the same distance as the proximal end. The safety and reliability with which the doctor can guide the catheter are then greatly impaired.

It is desirable that a catheter of this type can also be used according to the so-called monorail system. With this system which is described in European Patent 203,945, the guide wire which is guided from the tip inside the catheter does not come out of the shaft at the proximal end of the catheter but instead comes out of the shaft at a certain short distance from the balloon. This facilitates changing catheters while the guide wire is in the blood vessel with its end after the occlusion. Without this outlet opening a short distance from the balloon, i.e., without the monorail system, the guide wire would have to project out of the patient's body for a length at least equal to the total catheter length. With the monorail system the guide wire can be much shorter and changing catheters is easier and faster accordingly. Less effort in manipulation is required to keep the guide wire that projects out of the patient's body sterile, and the catheter need not be advanced over a guide wire approximately 3 meters long, for example.

SUMMARY OF THE INVENTION

The present invention is directed toward a balloon catheter comprising a shaft having proximal and distal ends and a wall extending therebetween, with a balloon being located proximate the distal end, the shaft comprising a proximal area including a first tubular member having a plurality of passageways being disposed therein, with one of the passageways being a first lumen for supplying fluid to the balloon, and a distal area including a second tubular member having a plurality of passageways being disposed therein, with one of the passageways of the distal area having a second lumen for receiving a guide wire, the proximal area being more rigid than the distal area, and an opening being disposed in the wall of the shaft in the proximal area, with the opening being adapted to receive the guide wire for passage therethrough and into the second lumen.

The present invention is based on the problem of making available a balloon catheter of the type described initially that is simple to manufacture and can be used universally according to the monorail system, but with the rigidity of its shaft not diminished by the outlet opening which then must be provided for the guide wire. This problem is solved by the fact that an outlet opening for the guide wire is provided in the side of the shaft of the catheter and this opening is arranged in the proximal shaft area 7here the shaft is more rigid and has a coaxial arrangement.

This accomplishes the result that the catheter can be used according to the monorail system. At the same time, the opening for the guide wire causes the least possible weakening of the catheter shaft. In the biaxial area of the shaft, a passage for the guide wire can be produced more easily due to the fact that only one wall need be punctured to create an opening, but then a larger hole in the shaft would be a sensitive problem for the shaft structure. Because of the shaft structure here and the soft material selected for this area, the shaft is least rigid here. Providing an opening in the shaft structure in this area would further reduce the rigidity of the shaft in precisely the area 7here the shaft already is least rigid. Then the shaft would buckle at this point and serious problems could occur in retracting the catheter from the vessel. Instead of the biaxial shaft area where it would be easier to create the opening, however, the opening is provided in the coaxial area where the material of the shaft is more rigid and thus more resistant to buckling, and the shaft structure is more stable due to the fact that four walls are provided in the longitudinal section. Another advantage is that with this arrangement the passage for the guide wire is located proximally from the connection between the proximal and distal portions of the shaft that is sensitive to buckling. This means that the guide wire is also available as an additional reinforcement for this area which is at risk. It bridges the critical transition between the flexible area of the shaft and the rigid area of the shaft. Finally, another advantage is that with the arrangement according to this invention, the outlet opening can be enlarged with no problem to the extent that the guide wire easily comes out of the opening when threaded into the catheter. Then no aid devices need be incorporated into the lumen of the guide wire to facilitate the guide wire coming out of the lumen.

In one embodiment of this invention, the guide wire lumen extends from the outermost proximal end of the catheter to the outermost distal end of the catheter 7ithout interruption. This lumen can then be used to advantage in other areas, e.g., to hold an additional removable and optionally shapeable guide wire for transporting fluids such as contrast media, solutions for reducing blood coagulation, etc., and it can also be used for pressure measurements. It is important that this measure provides an opportunity to insert a new guide wire without any change in the position of the catheter when the guide wire used previously has been accidentally removed from the outlet opening.

In another embodiment of this invention, a sheathing segment of the wall of the guide wire lumen is attached to the wall of the balloon lumen in such a way as to provide a seal in the area of the outlet opening for the guide wire, and in order to create the outlet opening within the segment that is connected with a seal, both the wall of the balloon lumen and the wall of the guide wire lumen are punctured. This yields an outlet opening that is especially simple to produce, and the guide wire tubing merely comes in contact with the wall of the shaft instead of puncturing it. At the same time, by doubling the wall thickness in the area of contact, the strength of the catheter shaft is reinforced precisely where a reinforcement is necessary because of the outlet opening. Thus, the invention in this embodiment means not only that in conjunction with the outlet opening a weakened section is prevented in the part of the catheter that is already weaker, but also that the expected weakening is compensated by a reinforcement before it even occurs.

In yet another embodiment, the outlet opening for the guide wire in the coaxial shaft area is connected to the connection between the proximal and distal areas of the shaft. This measure leads to the result that the monorail guide wire lumen, namely the guide wire lumen between the outlet opening and the distal end of the catheter, remains relatively short. The development of thinner and thinner balloon catheters and progressively more flexible distal catheter areas has resulted in the fact that even more remote occlusions in blood vessels can be treated. This in turn leads to the result that the distal, more flexible areas of the catheter are now designed so they are longer. However, it is in the interest of easy handling with the help of this monorail system, as mentioned initially, if the monorail guide wire lumen remains relatively short. The measure described here is an advantageous compromise in this regard in that the base of the distal flexible shaft area preferably remains within the guide catheter that is in the aorta, but its end extends into the mouth of the coronary vessels during use. The arrangement of the outlet opening at the connection assures that the guide wire is always guided outside the guide catheter in the guide wire lumen and inside the catheter beyond the outlet opening in the guide catheter. A balloon catheter of this type is also simple to produce because the connection between the two tubing walls in the coaxial area can be created simultaneously with the connection of the coaxial shaft area with the biaxial shaft area.

When the outlet opening for the guide wire is produced by a cut in the axial direction through both walls, namely the wall of the balloon supply lumen and the wall of the guide wire lumen, this further simplifies the production of the balloon catheter. Relatively large cut pieces are produced by cutting rather than by drilling or grinding. Such large pieces are easier to dispose of, which is an aspect that becomes important when production takes place in a clean room, for example. A cut in the axial direction results in an elongated oval opening in the shaft, which allows an oblique passage of the guide wire through the opening without causing too sharp a deflection in the guide wire. By tapering the cut in both directions, stress peaks in the shaft are prevented.

There is one specially adapted method of producing a balloon catheter according to this invention, namely a process for creating an outlet opening for a guide wire in a balloon catheter having a shaft and a plurality of lumens comprising:

providing a filling that fills out a first of the lumens in an area of intended outlet opening;

providing a filling in a second of the lumens that presses a wall of the first lumen against a wall of the second lumen in the area of intended outlet opening;

supplying a heat-shrink element about the shaft in the area of intended outlet opening;

applying energy to shrink the heat-shrink element;

joining the wall of the first lumen to the wall of the second lumen;

removing the filling from each of the first and the second lumens; and creating the outlet opening by puncturing the joined walls to provide an opening through which the guide wire may pass.

DETAILED DESCRIPTION OF THE PREFERRED EMBODIMENTS

Figure 1:
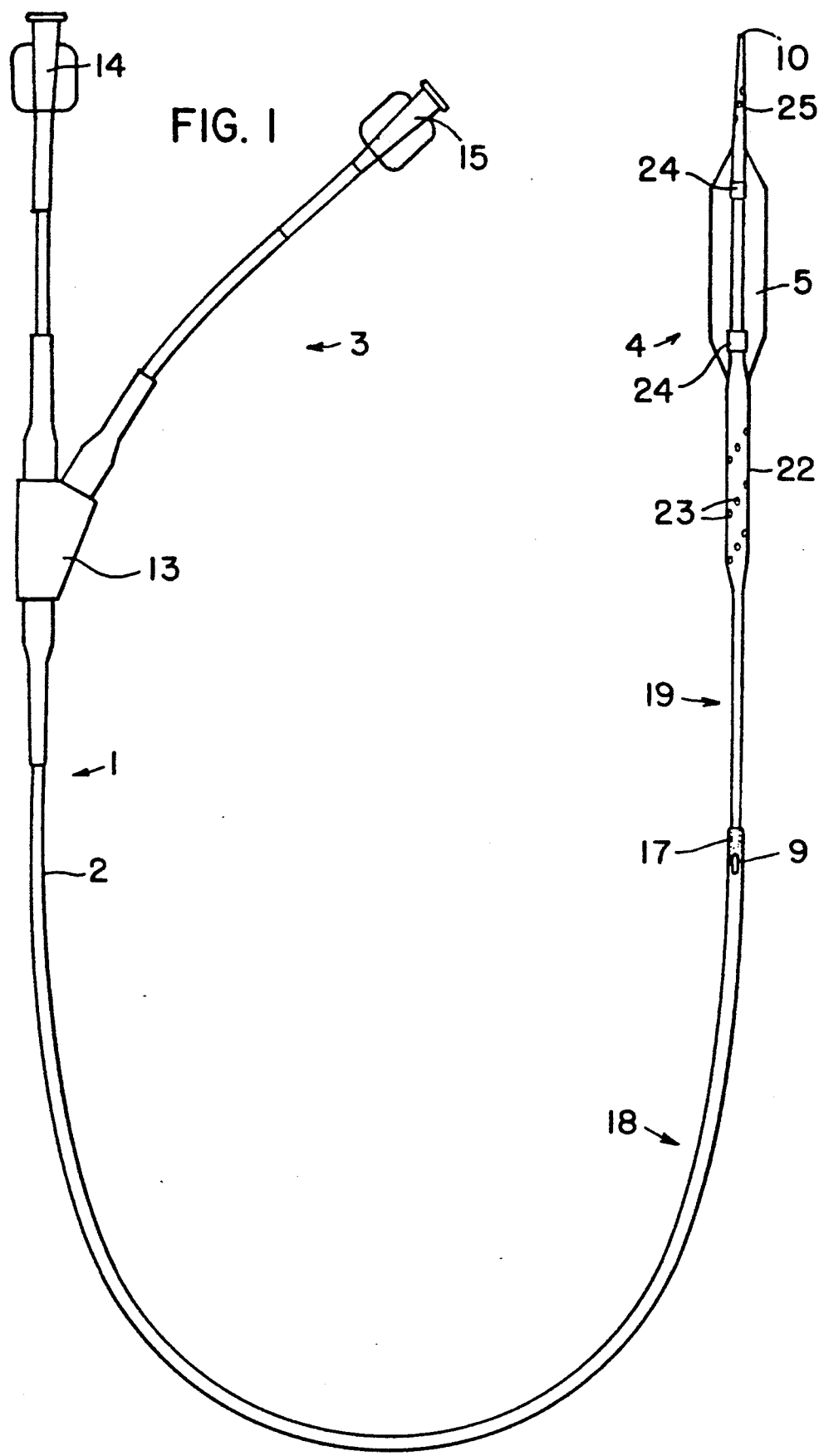
FIG. 1 is a schematic view of a balloon catheter in accordance with the principles of the present invention.

The description herein presented refers to the accompanying drawings in which like reference numerals refer to like parts throughout the several views.

FIG. 1 shows a balloon catheter 1 with a shaft 2. The proximal end of the catheter 3 is where the catheter is manipulated. The distal end of the catheter 4 is the opposite end.

A balloon 5 that can be inflated with a fluid until it is taut is provided on the distal end 4 of catheter 1. Shaft 2 has for this purpose two channels known generally as lumens, one lumen 6 for supplying the balloon (see FIGS. 3 to 6) and one lumen 7 for the guide wire 8.

Figure 2:
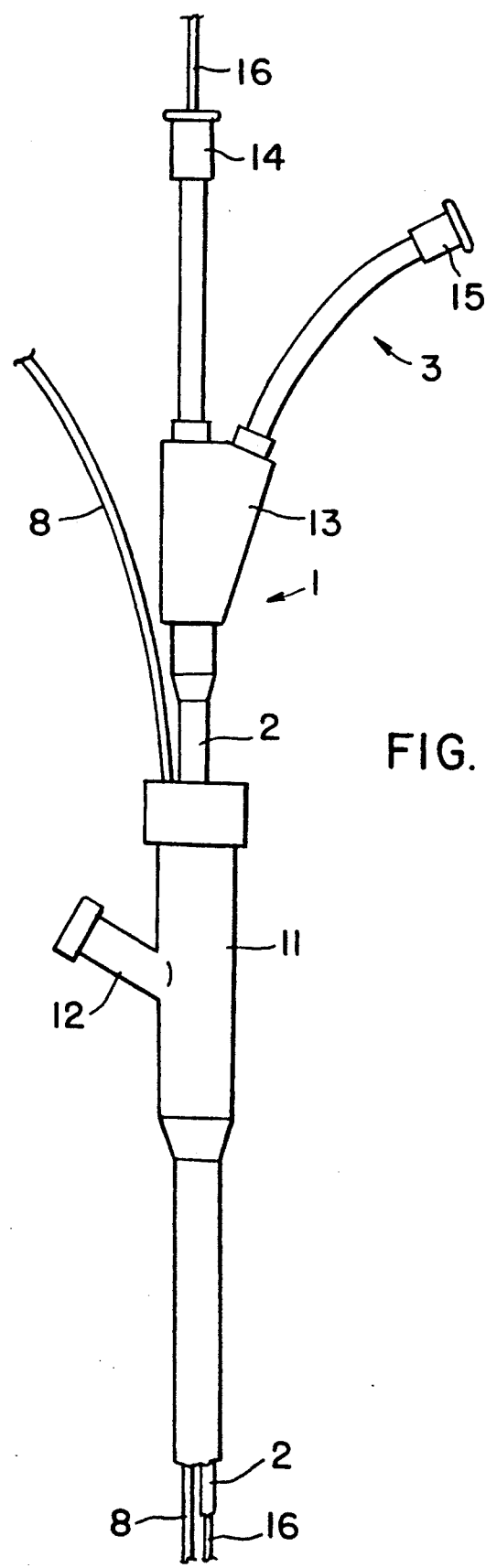
FIG. 2 is an enlarged, schematic representation of a proximal end of a balloon catheter, much like the catheter depicted in FIG. 1, and further including a guide catheter, a guide wire and a removable reinforcing wire.

As shown in FIG. 2, the balloon catheter 1 is used together with guide wire 8. Guide wire 8 is inserted together with catheter 1 or in front of catheter 1 into the blood vessel. Guide wire 8 is designed so it is steerable, i.e., it may have a certain curved shape at the tip, or the doctor may create a certain curved shape to 7hich it always returns when no force is acting on it. At the same time, the guide wire has torsional rigidity. With these two properties, the guide wire can be advanced in straight vascular sections and can be guided into branches due to the shape of the tip, but it can also be guided reliably past branches in the vessel by twisting the proximal end of the wire so the curved shape at the tip of the wire is twisted away from the branch and toward the other side of the vessel.

Guide wire 8 is used in the form shown in FIG. 2 according to the so-called monorail principle disclosed in European Patent 203,945. This means that guide wire 8 is first parallel to catheter 1 and outside it as seen from the proximal end 3 of catheter 1. At opening 9 in FIG. 1, guide wire 8 which is not shown in FIG. 1 enters catheter 1 and is guided from there inside catheter 1, leaving catheter 1 at the tip 10 of the catheter at the distal end of balloon 5. FIG. 2 also shows guide catheter 11 in addition to guide wire 8. Guide catheter 11 surrounds catheter 1 and guide wire 8 from the outside and serves as a guide for both of them over a rather long segment of the vessel. At its proximal end, guide catheter 11 surrounds catheter 1 and guide wire 8 with a rubber gasket (not shown) on the inside. A side connection 12 is provided on the side of guide catheter 11 and is used for adding contrast media or medication to prevent coagulation of blood or it may serve for performing pressure measurements.

As shown in FIGS. 1 and 2, a branch 13 is provided on the proximal end 3 of catheter 1. In this branch 13, one lumen of catheter 1 is guided into connection 14 with a seal. The other lumen opens into a sealed space inside branch 13, from which the second connection 15 diverges. In FIG. 2 a removable reinforcing wire 16 is inserted into one lumen through connection 14. Removable reinforcing wires are used to provide additional reinforcement of the proximal area of the catheter at least as long as the corresponding lumen is not used to the full extent for some other purpose.

Figure 5:
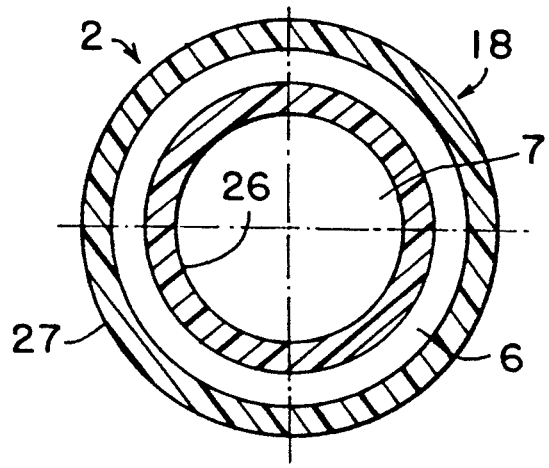
FIG. 5 is an enlarged, cross-sectional view of the proximal area of the catheter shaft of FIG. 1 with the view being located proximally of the guide wire outlet opening.

Shaft 2 of catheter 1 in FIG. 1 is composed of a proximal shaft area 18 and a distal shaft area 19 at connection 17. In the proximal area 18 the shaft is made of a more rigid material. A cross section through the shaft in the proximal area is shown in FIG. 5, where it is apparent that in this area of shaft 2 the lumen 7 for guide wire 8 is guided coaxially in the shaft according to the "tube-in-a-tube" system. Lumen 6, in a ring shape through which balloon 5 is supplied, surrounds lumen 7 for guide wire 8. This design also makes shaft 2 rigid because four walls are thus available in the longitudinal section in order to contribute to its flexural rigidity.

Figure 8:
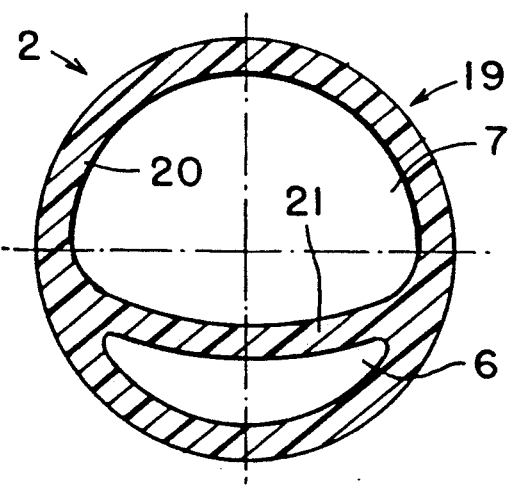
FIG. 8 is an enlarged, cross-sectional view of the catheter shaft taken in the distal area of the shaft.

In the distal area 19, the shaft is made of a more flexible material than in the proximal area 18. A cross section through the shaft in the distal area 19 is shown in FIG. 8. Lumen 6 for supplying the balloon and lumen 7 to receive the guide wire 8 are arranged biaxially side by side with separate axes. A joint shaft sheathing 20 surrounds both lumens which are separated only by dividing wall 21.

Between the connection 17 and balloon 5 and following balloon 5, shaft 2 is further calibrated in the distal shaft area for a certain length 22 so that the guide wire lumen there has a larger diameter. Along this length 22 several small holes 23 are provided in shaft 2 leading into the guide wire lumen 7. These holes are so small that they do not lessen the strength of shaft 2, but at the same time they allow enough blood to pass through without leading to a blockage.

Within balloon 5 the balloon supply lumen 6 is cut open and has been removed completely, so only the guide wire lumen 7 continues beyond the balloon toward catheter tip 10. Gold markings 24 on the shaft inside balloon 5 show clearly the position of balloon 5 in an x-ray. Balloon 5 is produced separately and then is subsequently attached to the shaft, e.g., by welding. At the distal end of balloon 5 only the portion of shaft 2 that remains after removing the balloon supply lumen 6, namely the part of the shaft surrounding guide wire lumen 7, comes out of the balloon.

In this shaft area at the distal end of balloon 5, there are again small holes 25. Due to the holes 23 and 25 and the guide wire lumen 7 which is calibrated with a larger diameter, a connection is established from the proximal side of balloon 5 to the distal side of balloon 5 through guide wire lumen 7. A certain flow of blood through this connection is possible even when guide wire 8 is placed in the guide wire lumen 7. The blood flow is increased accordingly when the guide wire 8 is retracted from length 22. This blood flow can supply blood to the vessels located distally from the balloon. This is an important factor because this makes it possible to lengthen the treatment of the occlusion in the vein without any negative effects on the organs located distally from the balloon due to the great reduction in circulation.

When guide wire 8 is retracted from length 22 in order to facilitate blood flow in lumen 7, the guide wire should not be inadvertently removed from opening 9. The function of guide wire 8 would then be lost. Therefore, it is advantageous if, as shown in the practical example, a definite distance is maintained between the length 22 and the opening 9, e.g., on the order of half the length of the distal shaft area 19. As a rule, however, it is sufficient if this distance is approximately as long as the length 22 itself.

Figure 3:
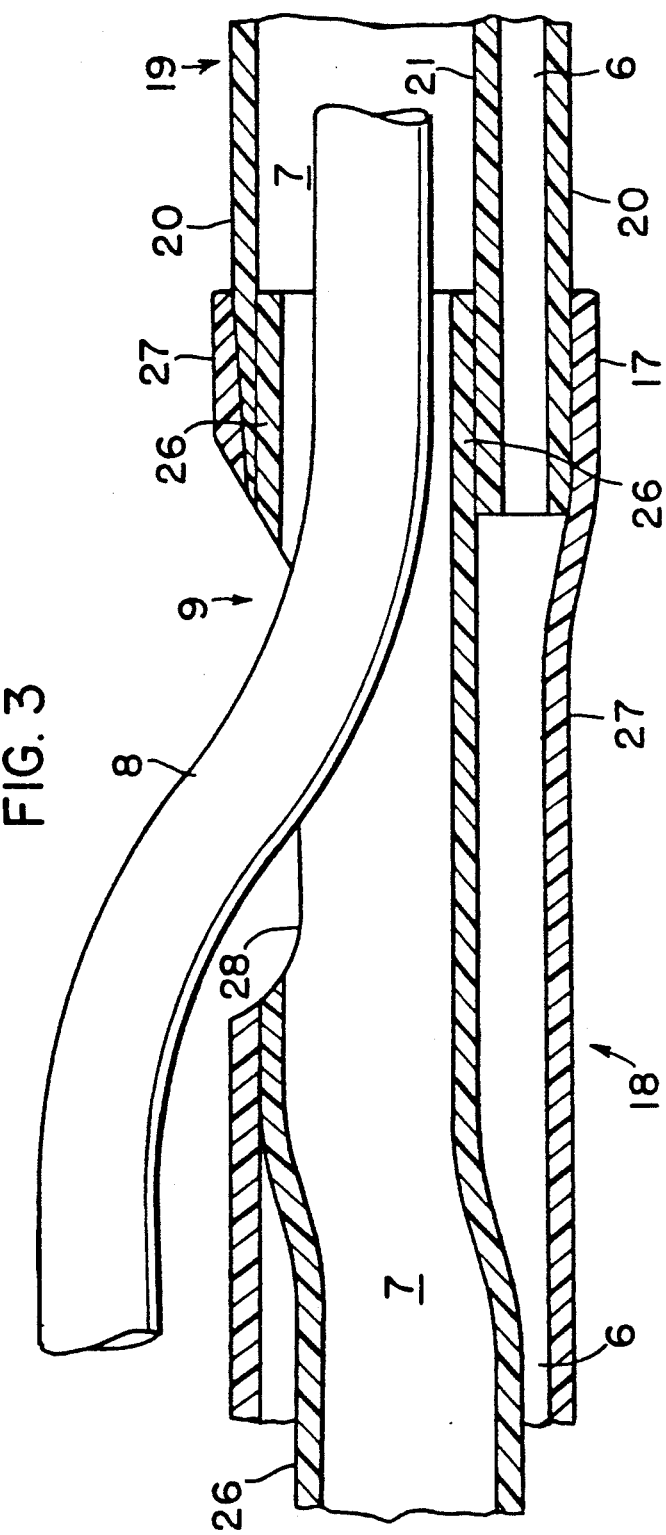
FIG. 3 is an enlarged, sectional view of a portion of the catheter of FIG. 1 showing a guide wire outlet opening and including a guidewire passing through the opening.
Figure 7:
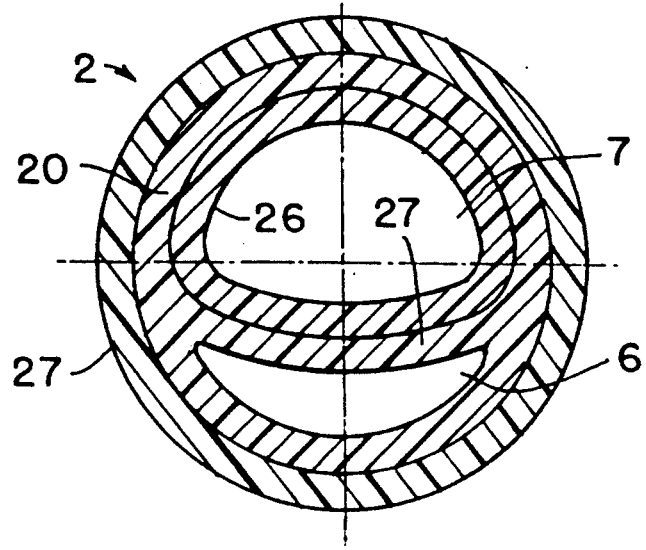
FIG. 7 is an enlarged, cross-sectional view of the catheter shaft at the connection location where the proximal and distal areas of the shaft are joined.

The connection 17 between the proximal, more rigid shaft area 18, and the distal, more flexible shaft area 19, is shown in detail in FIGS. 3 and 7. The inside tube 26 of the coaxial proximal shaft area 18 is inserted into the guide wire lumen 7 of the biaxial distal shaft area 19. Thus, the guide wire lumen 7 extends without interruption from the outermost proximal end of catheter 1 to the outermost distal end of the catheter. The outer tubing 27 is pushed over the shaft sheathing 20 of the biaxial distal shaft area 19. The two shaft areas are then joined together through the use of a binder or by welding. One advantageous method consists of providing the lumens with a filling and surrounding the connection 17 with a fitting shrinkable tubing. When the shrinkable tubing is selected appropriately, the supply of heat is just enough to shrink it so the two shaft areas are pressed together in shrinkage of the heat shrink tubing and are welded together at the same time. Then the heat-shrink tubing can be removed again.

Figure 4:
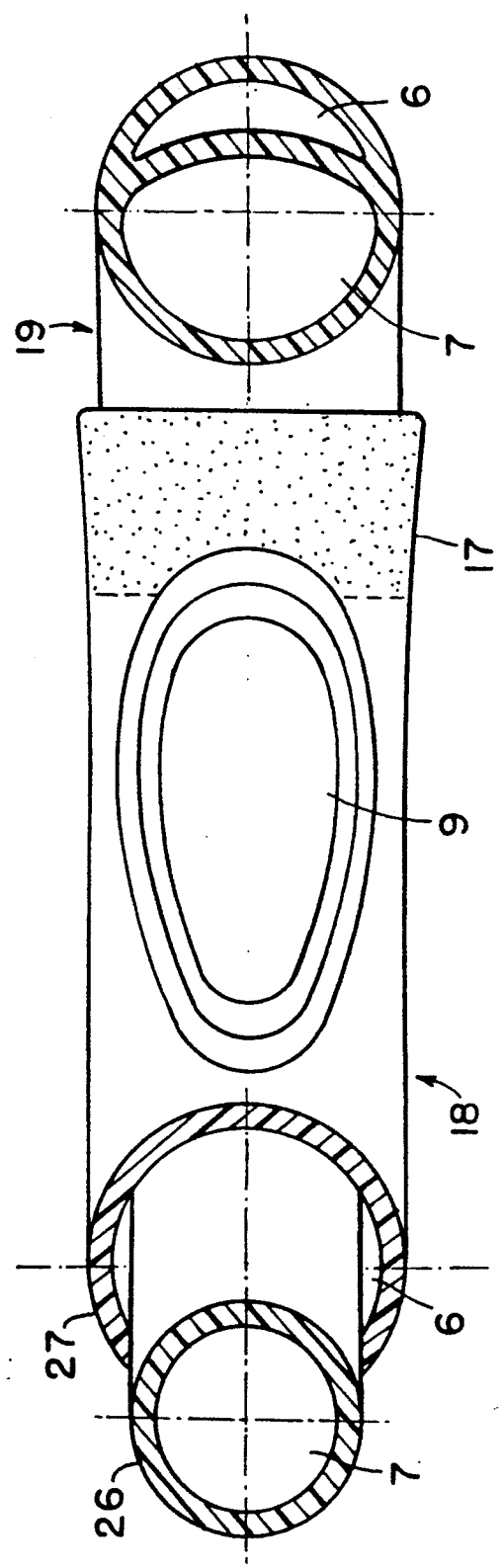
FIG. 4 depicts an enlarged, schematic view of the guidewire opening of FIG. 1 and additionally includes a connection coupling the proximal area of the catheter shaft to the distal area of the catheter shaft and further illustrates sectional views, taken at oblique angles, of the proximal and distal areas of the shaft.
Figure 6:
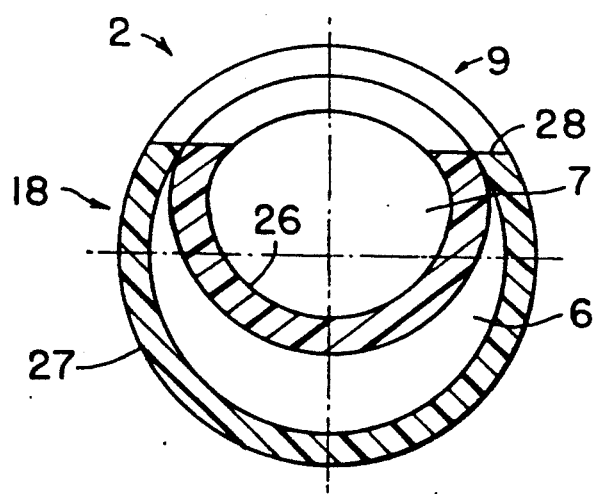
FIG. 6 is an enlarged, cross-sectional view of the catheter shaft at the guide wire outlet opening.

The side opening 9 in shaft 2 for guide wire 8 is shown in detail in FIGS. 3, 4 and 6. These figures show that the outlet opening 9 for guide wire 8 is not located in the distal shaft area 19 where the shaft 2 is biaxial, but instead is arranged in the proximal shaft area 18 where the shaft 2 is coaxial and more rigid.

FIG. 6, in particular, shows that a sheathing segment of the wall of guide wire lumen 7, i.e., a sheathing segment of the inside tubing 26, is connected to the wall of balloon lumen 6, i.e., the outer tubing 27, so as to form a seal in the area of the outlet opening 9 for guide wire 8. To create outlet opening 9 inside the segment that is connected with a seal, the wall of balloon lumen 6, the outer tubing 27, and the wall of guide wire lumen 7, the inside tubing 26, are punctured by a cut 28. Cut 28 is continued in the axial direction and punctures both walls, namely the wall of the balloon supply lumen and the wall of the guide wire lumen at the same time. It thus surrounds an elongated oval hole as shown in FIG. 4. The shape of the cutout thus produced does not lead to any stress peaks in the catheter shaft. This cutout shape may be so large and so long that guide wire 8 easily comes out of shaft 1 when threaded into the catheter without requiring devices such as a ramp, etc., in lumen 7 to facilitate the catheter coming out of the shaft. Outlet opening 9 for guide wire 8 in the coaxial proximal shaft area 18 is as close as possible to the connection 17 between the proximal shaft area 18 and the distal shaft area 19, so the connection 17 and the seal for the outlet opening 9 can be created in one operation.

An especially suitable method of producing an outlet opening for the guide wire in a balloon catheter according to this invention consists in providing guide wire lumen 7 with a filling such as a tubing of a suitable plastic that fills out the lumen 7 in the area of the intended outlet opening 9, providing the balloon supply lumen 6 with a filling such as a profile section of a suitable material that presses tubing 26 for guide wire 8 against tubing 27 from the inside in the area of outlet opening 9 in the wall of the balloon supply lumen 6, surrounding shaft 2 with a heat-shrink tubing in the area of the intended outlet opening 9, initiating shrinkage of the heat-shrink tubing by applying heat, joining the walls of guide wire lumen 7 and balloon supply lumen 6 that are pressed together by the fillings on the inside and the heat-shrink element on the outside in the area of the intended outlet opening 9 by thermal means, e.g., by welding or by means of a binder, removing the fillings again, removing the heat-shrink tubing and creating outlet opening 9 by puncturing the combined walls of both the guide wire lumen 7, i.e., tubing 26, and balloon lumen 6, i.e., tubing 27, with a cut 28.

I claim:

1. A balloon dilatation catheter, comprising:
    a proximal shaft with a proximal end and a distal end having an inner tube defining a first lumen and a coaxial outer tube defining a second annular lumen between the inner tube and the outer tube;
    a bilumen distal shaft defining a third and fourth lumen with a proximal end and a distal end, wherein the proximal end of the bilumen distal shaft is connected to the distal end of the proximal shaft such that the first lumen is in communication with the third lumen to define a guidewire passageway and the second lumen is in fluid communication with the fourth lumen to define a balloon inflation passageway, wherein a distal portion of the inner tube is bonded directly to a distal portion of the outer tube to thereby block at least a portion of the second lumen;
    a balloon coaxially disposed around the bilumen distal shaft and in fluid communication with the fourth lumen; and
    a proximal guidewire port extending through the bonded distal portions of the inner tube and the outer tube in communication with the first lumen and the third lumen.

2. The balloon dilatation catheter of claim 1 wherein the proximal shaft is stiffer than the distal bilumen shaft.

3. The balloon dilatation catheter of claim 1 wherein the distal bilumen shaft defines a plurality of perfusion ports proximal and distal of the balloon and in communication with the third lumen.

4. The balloon dilatation catheter of claim 2 wherein the distal bilumen shaft defines a plurality of perfusion ports proximal and distal of the balloon and in communication with the third lumen.

* * * * *